(12) United States Patent
Gupta

(10) Patent No.: US 8,383,033 B2
(45) Date of Patent: Feb. 26, 2013

(54) METHOD OF BONDING POROUS METAL TO METAL SUBSTRATES

(75) Inventor: Gautam Gupta, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 251 days.

(21) Appl. No.: 12/575,998

(22) Filed: Oct. 8, 2009

(65) Prior Publication Data

US 2011/0085929 A1 Apr. 14, 2011

(51) Int. Cl.
*B22F 7/04* (2006.01)
(52) U.S. Cl. .................. 419/8; 419/2; 419/36
(58) Field of Classification Search .............. 419/8, 36
See application file for complete search history.

(56) References Cited

U.S. PATENT DOCUMENTS

| | | | |
|---|---|---|---|
| 3,855,638 A | 12/1974 | Pilliar | |
| 4,156,943 A | 6/1979 | Collier | |
| 4,206,271 A | 6/1980 | Norling et al. | |
| 4,309,488 A | 1/1982 | Heide et al. | |
| 4,412,643 A | 11/1983 | Sato et al. | |
| 4,550,448 A | 11/1985 | Kenna | |
| 4,612,160 A | 9/1986 | Donlevy et al. | |
| 4,644,942 A | 2/1987 | Sump | |
| 4,846,393 A | 7/1989 | Devillard | |
| 4,854,496 A | 8/1989 | Bugle | |
| 4,957,819 A | 9/1990 | Kawahara et al. | |
| 5,027,998 A | 7/1991 | Bugle | |
| 5,047,182 A | 9/1991 | Sundback et al. | |
| 5,080,672 A | 1/1992 | Bellis | |
| 5,080,674 A | 1/1992 | Jacobs et al. | |
| 5,096,518 A | 3/1992 | Fujikawa et al. | |
| 5,104,410 A | 4/1992 | Chowdhary | |
| 5,126,103 A | 6/1992 | Ishizaki et al. | |
| 5,198,308 A | 3/1993 | Shetty et al. | |
| 5,201,766 A | 4/1993 | Georgette | |
| 5,282,861 A | 2/1994 | Kaplan | |
| 5,323,954 A | 6/1994 | Shetty et al. | |
| 5,348,788 A | 9/1994 | White | |
| 5,443,510 A | 8/1995 | Shetty et al. | |
| 5,504,300 A | 4/1996 | Devanathan et al. | |
| 5,507,824 A | 4/1996 | Lennox | |
| 5,535,810 A | 7/1996 | Compton et al. | |
| 5,688,453 A | 11/1997 | England et al. | |
| 5,702,458 A | 12/1997 | Burstein et al. | |
| 5,734,959 A | 3/1998 | Krebs et al. | |
| 5,926,685 A | 7/1999 | Krebs et al. | |
| 6,022,509 A | 2/2000 | Matthews et al. | |
| 6,066,176 A | 5/2000 | Oshida | |
| 6,132,674 A | 10/2000 | Compton et al. | |
| 6,206,924 B1 | 3/2001 | Timm | |
| 6,458,161 B1 | 10/2002 | Gibbs et al. | |
| 6,495,448 B1 | 12/2002 | Lee | |
| 6,527,809 B1 | 3/2003 | Doursounian et al. | |
| 6,544,472 B1 | 4/2003 | Compton et al. | |
| 6,605,648 B1 | 8/2003 | Johnson et al. | |
| 6,660,224 B2 | 12/2003 | Lefebvre et al. | |
| 6,913,623 B1 | 7/2005 | Zhu | |
| 6,945,448 B2 | 9/2005 | Medlin et al. | |
| 7,147,819 B2 | 12/2006 | Bram et al. | |
| 7,291,177 B2 | 11/2007 | Gibbs | |
| 7,351,371 B2 | 4/2008 | Nelles et al. | |
| 7,597,715 B2 | 10/2009 | Brown et al. | |
| 7,635,447 B2 | 12/2009 | Hamman et al. | |
| 7,713,306 B2 | 5/2010 | Gibbs | |
| 7,883,661 B2 | 2/2011 | Hamman et al. | |
| 2002/0062154 A1 | 5/2002 | Ayers | |
| 2003/0083741 A1 | 5/2003 | Woo et al. | |
| 2003/0153981 A1 | 8/2003 | Wang et al. | |
| 2003/0171820 A1 | 9/2003 | Wilshaw et al. | |
| 2003/0200837 A1 | 10/2003 | Matsuura et al. | |
| 2003/0220696 A1 | 11/2003 | Levine et al. | |
| 2003/0232124 A1 | 12/2003 | Medlin et al. | |
| 2004/0064192 A1 | 4/2004 | Bubb | |
| 2004/0072010 A1 | 4/2004 | Date et al. | |
| 2004/0109853 A1 | 6/2004 | McDaniel | |
| 2004/0137218 A1 | 7/2004 | Liu et al. | |
| 2005/0031704 A1 | 2/2005 | Ahn | |
| 2005/0048193 A1 | 3/2005 | Li et al. | |
| 2005/0100470 A1 | 5/2005 | Lefebvre et al. | |
| 2005/0145364 A1 | 7/2005 | Nakajima | |
| 2005/0184134 A1 | 8/2005 | Charlebois et al. | |
| 2005/0234559 A1 | 10/2005 | Fernandez et al. | |
| 2005/0242162 A1 | 11/2005 | Medlin et al. | |
| 2006/0002810 A1 | 1/2006 | Grohowski, Jr. | |
| 2006/0018942 A1 | 1/2006 | Rowe et al. | |
| 2006/0241776 A1 | 10/2006 | Brown et al. | |
| 2006/0241781 A1 | 10/2006 | Brown et al. | |
| 2007/0129809 A1 | 6/2007 | Meridew et al. | |
| 2007/0150068 A1 | 6/2007 | Dong et al. | |
| 2007/0173948 A1 | 7/2007 | Meridew et al. | |
| 2007/0196230 A1 | 8/2007 | Hamman et al. | |
| 2007/0243312 A1 | 10/2007 | Bulko | |
| 2007/0250175 A1 | 10/2007 | Meridew et al. | |

(Continued)

FOREIGN PATENT DOCUMENTS

| DE | 3130732 | 5/1983 |
|---|---|---|
| DE | 19726961 | 11/1998 |

(Continued)

OTHER PUBLICATIONS

Bram et al. "High-Porosity Titanium, Stainless Steel, and Superalloy Parts" Advanced Engineering Materials, vol. 2, No. 4 (2000) pp. 196-199.

(Continued)

*Primary Examiner* — Roy King
*Assistant Examiner* — Ngoclan T Mai
(74) *Attorney, Agent, or Firm* — Harness, Dickey

(57) ABSTRACT

A method for preparing an implant having a porous metal component. A loose powder mixture including a biocompatible metal powder and a spacing agent is prepared and compressed onto a metal base. After being compressed, the spacing agent is removed, thereby forming a compact including a porous metal structure pressed on the metal base. The compact is sintered, forming a subassembly, which is aligned with a metal substrate portion of an implant. A metallurgical bonding process, such as diffusion bonding, is performed at the interface of the subassembly and the metal substrate to form an implant having a porous metal component.

17 Claims, 5 Drawing Sheets

U.S. PATENT DOCUMENTS

| | | | |
|---|---|---|---|
| 2007/0264152 A1 | 11/2007 | Zhao | |
| 2008/0027556 A1 | 1/2008 | Metzger | |
| 2008/0147187 A1 | 6/2008 | Bollinger et al. | |
| 2008/0195222 A1* | 8/2008 | Rauguth et al. | 623/23.6 |
| 2008/0199343 A1 | 8/2008 | Rust et al. | |
| 2009/0084491 A1 | 4/2009 | Uthgenannt et al. | |
| 2009/0098310 A1* | 4/2009 | Hippensteel et al. | 427/576 |
| 2010/0004754 A1 | 1/2010 | Brown et al. | |
| 2010/0074789 A1* | 3/2010 | Heuer et al. | 419/8 |

FOREIGN PATENT DOCUMENTS

| | | |
|---|---|---|
| EP | 1421918 | 5/2004 |
| JP | 3837502 | 8/2006 |
| WO | WO 2004/080340 | 9/2004 |
| WO | WO 2006/007861 | 1/2006 |

OTHER PUBLICATIONS

Laptev, A. et al. "Study of Production Route for Titanium Parts Combining Very High Porosity and Complex Shape" Powder Metallurgy, vol. 47, No. 1 (2004) pp. 85-92.

Oliveira et al. "Porous Structure Characterization in Titanium Coating for Surgical Implants" Materials Research, vol. 5, No. 3 (2002) pp. 269-273.

Wen, C.E. et al. "Novel Titanium Foam for Bone Tissue Engineering" J. Mater. Res., vol. 17, No. 10 (2002) pp. 2633-2639.

Wen, C.E. et al. "Processing and Mechanical Properties of Autogenous Titanium Implant Materials" Journal of Materials Science: Materials in Medicine 13 (2002) pp. 397-401.

Wen, C.E. et al. "Processing of Biocompatible Porous Ti and Mg" Scripta Materialia 45 (2001) pp. 1147-1153.

Wheeler, K.R. et al. "Porous Metals as a Hard Tissue Substitute. Part II: Porous Metal Properties" Biomat., Med. Dev., Art. Org., 1(2), (1973) pp. 337-348.

Li, J. et al. "A Novel Porous Ti6Al4V: Characterization and Cell Attachment" Journal of Biomedical Materials Research, vol. 73a, No. 2, pp. 223-233 (May 2005).

Mahoney, M. and Bampton, C. "Fundamentals of Diffusion Bonding" ASM Handbook, vol. 6 (1994), pp. 156-159.

* cited by examiner

METHOD OF BONDING POROUS METAL TO METAL SUBSTRATES

INTRODUCTION

The present technology relates to medical implants containing a porous metal component and methods of their manufacture. In the growing field of medical devices, there is continued need to provide lightweight orthopedic implants having enhanced strength, such as implants with porous metal that can provide a three-dimensional space for bone in-growth.

Joining porous metal to a metal substrate for use with an implant can be challenging, however, because the contact points available at the interface of the materials may be limited due to the surface morphology of the porous metal construct. While various methods are known for joining powder metal materials to a metal substrate, such as sintering, welding, and brazing, there are many drawbacks. The high temperatures of sintering may affect substrate properties. Welding and brazing typically use filler materials that can adversely affect biocompatibility of the final device for medical applications. Thus, it would be desirable to provide a method for joining powder metal to an implant that operates at a lower temperature and does not require additional filler materials. Specifically, it is desirable to use diffusion bonding techniques to join a porous metal structure to a metal substrate for use in an implant.

SUMMARY

The present technology provides methods for preparing an implant having a porous metal component. In various embodiments, the method includes preparing a loose powder mixture including a biocompatible metal powder and a spacing agent. The powder mixture is compressed onto a metal base. After being compressed, the spacing agent is removed, thereby forming a compact, which comprises a porous metal structure pressed on the metal base. The method includes sintering the compact, forming a subassembly having a porous metal component and a metal base, and aligning the subassembly with a metal substrate component of the desired final implant. A metallurgical bond is formed between the subassembly and the metal substrate component. In various embodiments, the metal base of the subassembly is diffusion bonded to the metal substrate to form an implant having a porous metal component.

In other embodiments, the method for preparing an implant having a porous metal component includes preparing a loose powder mixture comprising a biocompatible metal powder and a spacing agent, and compressing the powder mixture onto a metal base defining a metal surface. The metal base can be from a solid stock of metal material or can be a layer of powder metal material. The powder mixture is heated to remove the spacing agent and to define a plurality of pores therein, forming a compact. The compact is then sintered, forming a subassembly including a porous metal structure having a metal backing. The metal backing of the subassembly is then aligned with a metal substrate component of the desired final implant. The method includes diffusion bonding the metal backing to the metal substrate to form an implant having a porous metal component.

Still in other embodiments, the method for preparing an implant having a porous metal component includes filling or otherwise placing a base layer comprising a biocompatible metal powder into a mold. A loose powder mixture of a biocompatible metal powder and a spacing agent is prepared. The method includes spreading the loose powder mixture into the mold on top of the base layer, forming a secondary layer. A compressive force is applied to the mold, thereby concurrently compressing the loose powder mixture of the secondary layer, compressing metal of the base layer, and pressing the secondary layer onto the base layer. The spacing agent is removed, defining a plurality of pores within the secondary layer. The method further includes sintering the mold contents and forming a subassembly including a porous metal structure having a powder metal backing. The powder metal backing of the subassembly is then diffusion bonded to a metal substrate portion of an implant, forming an implant having a porous metal component.

DRAWINGS

In the Figures, certain reference numerals indicate corresponding parts throughout the several views of the drawings.

Figure 1:
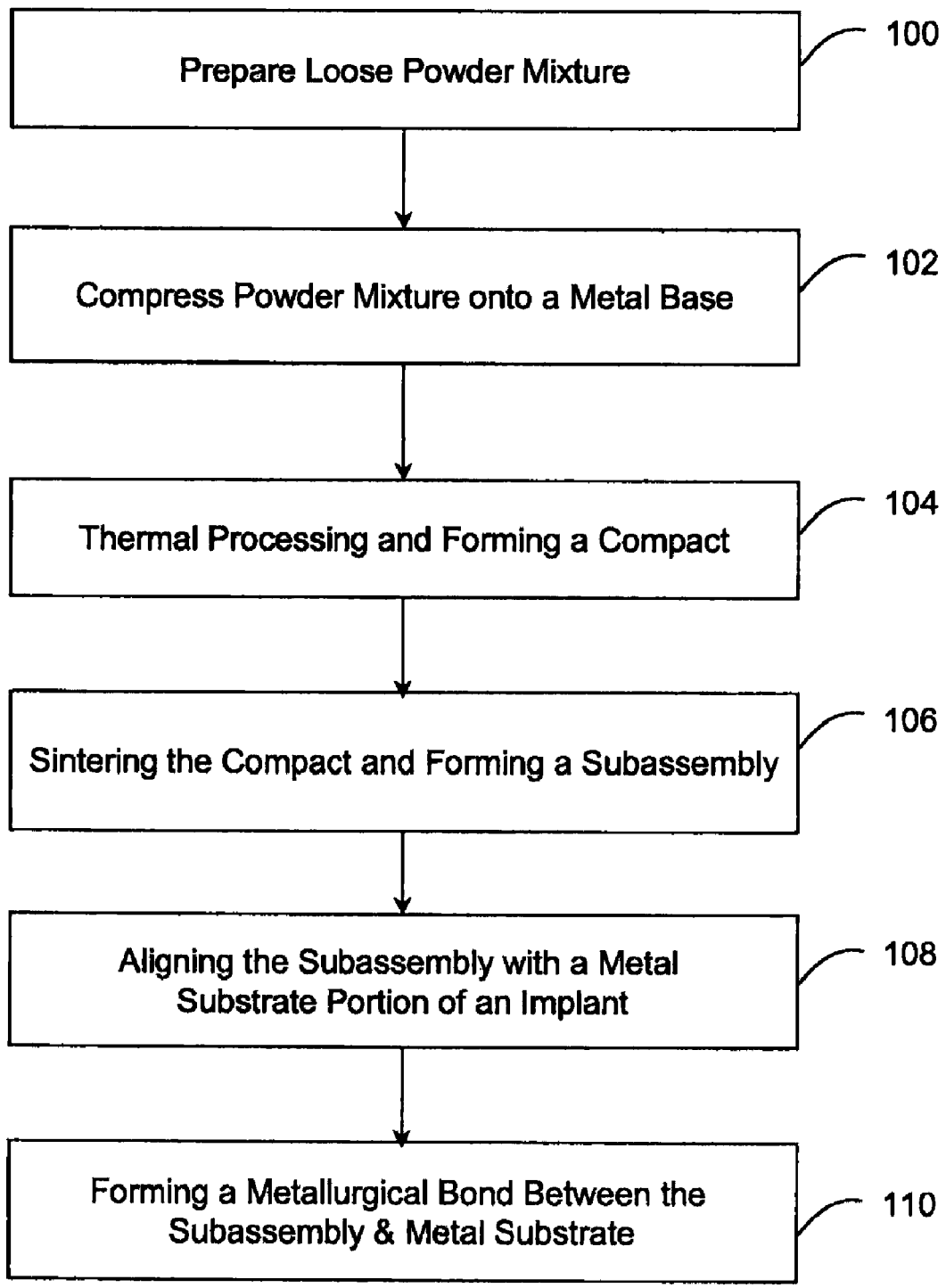
FIG. 1 is a flow diagram illustrating a method for preparing a porous metal implant.

It should be noted that the figures set forth herein are intended to exemplify the general characteristics of materials, methods and devices among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desirable", "preferred" and "preferably" refer to embodiments of the technology that afford certain benefits, under certain circumstances. However, other embodiments may also be preferred or desirable, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, Applicants specifically envision embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology provides methods for preparing a medical implant, including joining a porous metal component to a metal substrate of an implant. As used herein, the term "implant" may be used to refer to an entire implant, or a portion thereof. For example, an implant made in accordance with the present technology, having a porous metal component joined thereto, may constitute the entire implant, or it may be used with one or more other pieces or components that together form a final implant or implant assembly. One or more portions of the implant may be provided with a metal substrate external surface or the entire implant may define a continuous surface having a metal substrate. Generally, "joined" and "joining" are comprehensive terms used to describe all processes that affix one part to another. Many useful joining/welding processes provide the application of heat with controlled melting of base materials and a filler metal. Other useful joining processes rely on surface diffusion or solid state mechanical interlocking. Many options are available for specifically joining powder metal materials to a metal substrate portion of an implant, including sintering, various welding techniques, and brazing. However, the high temperatures of sintering may affect substrate properties, while the filler materials used in welding and brazing techniques can adversely affect biocompatibility of the final device for medical applications. For example, cobalt may melt at typical sintering temperatures.

With diffusion bonding (sometimes called sinter bonding), no additional materials are required to form a bond because the bonding relies on atomic diffusion between substrates. Accordingly, diffusion bonding techniques are attractive for biocompatible applications, providing a very clean solid state bond resulting from mechanical interlocking and alloy diffusion occurring at the joining interface of the mating components. Because diffusion bonding is conducted at lower temperatures, relative to sintering or welding, the formation of intermetallic eutectics at the joining interface is minimized or avoided altogether. In order to maintain strong and uniform bond strength, however, effective diffusion bonding may be limited by geometries. For example, the strength of a bond can be related to the number of contact points between the two mating components. Accordingly, joining a porous metal component directly to a metal substrate or a metal component of an implant by diffusion bonding can pose a problem because the number of contact points available at the joining interface between the two substrates may be limited to the particular surface morphology of the porous metal construct. Having such a limited contact area for bonding may make it difficult to achieve bonds strengths suitable for orthopedic applications.

The present technology provides methods for preparing a porous metal construct with a thin, integral, solid metal backing or metal base. As used herein, the terms "solid metal backing," "solid metal base," and "metal base" generally refer to a substantially non-porous metal backing, or base, that may include, as non-limiting examples, a solid metal or a compressed powder metal. This non-porous backing, or base, assists in creating a smooth surface-joining interface with an increased surface/contact area that yields a very strong, mechanically stable bond between the porous metal component and metal substrate portion of an implant when using diffusion bonding techniques.

With reference to FIG. 1, which generally depicts steps of various embodiments of the present technology, a loose powder mixture is in step 100. The loose powder mixture can comprise a biocompatible metal powder and a spacing agent, or porogen material. The metal powder can be any metal or alloy that is suitable for use as an implant and provides the desired strength and load bearing capabilities. Suitable exemplary metals include titanium, cobalt, chromium, or tantalum, alloys thereof, stainless steel, iron alloys, and combinations thereof. The metal powder particles can have a diameter ranging from between about 5 micrometers to about 1500 micrometers. In various embodiments, the metal powder particles have a diameter from between about 100 micrometers to about 500 micrometers, in other embodiments the metal powder particles can have a diameter from between about 75 micrometers to about 175 micrometers. The metal powder can be a mixture of at least two different particle sizes. For example, it may contain a first portion from a first mixture of metal particles having a diameter of between about 150 to about 250 micrometers and a second portion from a second mixture of metal particles having a diameter of between about 250 and about 425 micrometers. In certain embodiments, larger metal beads may be used.

In step 102, the loose metal mixture is compressed together and pressed onto a metal base. Such a metal base can be a solid metal, as will be discussed below. The chemical composition of the metal base can be identical to that of the metal powder, or the composition of the metal base can be different from that of the metal powder. In various embodiments, the compression of the powder mixture includes applying an isostatic pressing technique at ambient temperature, or using cold isostatic pressing (CIP). The CIP can use a water or air mixture pressurized up to the desired pressure range of from about 5,000 to about 100,000 psi. In various embodiments, the pressure range is from about 50,000 to about 75,000 psi, or about 60,000 psi.

The spacing agent, or porogen particles, of the loose powder mixture provides the pores of the porous metal implant. The spacing agent can be removable from the mixture and it may be desirable if the spacing agent does not leave residue in the porous metal implant. It may be further desirable that the spacing agent expands or contracts to supplement the formation of pores of a desired size within the porous metal implant. The pores may range in size of from between about 1 to about 1,000 micrometers, or as otherwise desired. For example, in certain embodiments, it may be desirable to have a pore size from about 100 to about 600 micrometers. In other embodiments, it may be desirable to have a pore size from between about 500 to about 700 micrometers. The spacing agent can be selected from the group consisting of hydrogen peroxide, urea, ammonium bicarbonate, ammonium carbonate, ammonium carbamate, calcium hydrogen phosphate, naphthalene, and mixtures thereof, or can be any other suitable subliming and space forming material. Generally, the spacing agent has a melting point, boiling point, sublimation temperature, etc. of less than about 400° C., or less than about 350° C., depending on the specific materials used.

A non-polar liquid binder can be used to improve the cohesiveness of the mixture because the non-polar liquid binder keeps all mixture components in close proximity and does not dissolve the spacing agent. The non-polar liquid binder can be a volatile compound with a boiling point sufficiently close to the sublimation or decomposition point of the spacing agent. In various embodiments, that temperature difference is less than about 200° C. In still other embodiments, that difference is less than about 100° C. The close range of the sublimation temperature of the spacing agent and the boiling point of the non-polar liquid binder allows for a single step removal of the spacing agent and the non-polar liquid binder during thermal processing.

The mixture of non-polar liquid binder, spacing agent, and metal powder can be made homogenous by mixing as is known in the art. In various embodiments, the ratio of metal powder to spacing agent can be from about 1:1 up to about 10:1, or greater. The non-polar liquid binder can be in a ratio of from about 1 part binder (in milliliters) to about 10 parts of solid (spacing agent and biocompatible metal powder, in grams) up to about 1 part binder 16 to about 30 parts of solid. Altering the ratios of the mixture components and/or the particle sizes of the components can provide an implant having a higher or lower porosity, enhanced load-bearing abilities, or can help to tailor the porous metal implant for a particular region of the body. Utilizing a ratio of metal powder to spacing agent of 8:1 will provide a dense implant having very fine pores. In another example, in a mixture having a 3:1 metal powder to spacing agent ratio, if the spacing agent has a diameter of at least about 25 micrometers and the metal powder has a diameter of about 10 micrometers, large pores result. If the metal powder and spacing agent diameter sizes were reversed, smaller pores would result.

As previously mentioned, the mixture can also include metal powders of different particulate sizes. By including metal powder particulates of at least two different sizes, a porosity gradient can be achieved. The porosity gradient can be such that the porosity of the implant increases or decreases by up to about 80% across the body of the implant. The porosity gradient can be continuous and scale up (or down) to a desired amount, or the porosity gradient can include differing porosity regions (e.g., 80% porosity region transitions to a 40% porosity region which transitions to a 75% porosity region). The transitions between the regions can be continuous in the porous metal implant. To provide the different porosities, a mixture corresponding to a particular porosity is stacked on top of or adjacent to a mixture having a different porosity.

With further reference to FIG. 1, once compressed and pressed onto the metal base, thermal processing is carried out and formation of a compact in step 104. The spacing agent provides the macroporosity and microporosity of the biocompatible metal powder before and during the initial thermal processing because after the spacing agent decomposes, pores or gaps remain between the metal powder particles where the spacing agent was located. The spacing agent particles can have a suitable particle diameter such that the final porosity of the porous metal portion is between about 65% to about 70%, or other porosity suitable for use with a medical implant.

The thermal processing step 104 includes removing the spacing agent and the non-polar liquid binder and forming a compact. In an exemplary method, the compact can be initially heated at from about 50° C. to about 350° C. or about 400° C. to remove the non-polar liquid binder and the spacing agent. The exact temperature can be selected depending on the combination of the non-polar liquid binder and the spacing agent, vacuum conditions, etc. It is desirable to remove the spacing agent at a temperature at which the metal does not react with the spacing agent. In various embodiments, that temperature can range from about 25° C. to about 500° C. In various other embodiments, that temperature can be a temperature less than the melting point of the metal powder. A suitable initial temperature can be at about at least 60° C. or higher, but preferably under the sintering temperature of the selected metal powder. It may be desirable for the initial temperature to be at about or above the boiling point or the sublimation point or decomposition of the binder component having the highest temperature value.

In step 106 the compact is sintered to create a subassembly including a porous metal structure and a metal base. As is known in the art, sintering creates metallic interparticle bonds that provide certain physical and mechanical properties of the porous metal implant. Sintering conditions (temperature, time, and atmosphere) should be such that the metallic interparticle bonds are created while extensive densification is avoided. The sintering can be performed in a controlled atmosphere, such as a vacuum (for example, at $10^{-5}$ torr) or under reduced pressure. It may be desirable to conduct the sintering in an inert atmosphere, for example, where the atmosphere is flushed with argon or helium gas prior to initiating the vacuum. Such a vacuum and/or the inert atmosphere will minimize or prevent solid solution hardening of the surface of the porous implant as a result of inward diffusion of oxygen and/or nitrogen into the metal and to prevent formation of oxides on the metal surface. The sintering process can occur using a single-oven or furnace process.

Sintering can be performed at once or in stages. A first sintering of the compact can be conducted to transform the compact (substantially free from metallurgical bonds between the metal powder particles) to the subassembly having metallurgical bonds. The temperature can be increased in a furnace or chamber (by 2° C., 5° C., 10° C., 20° C., 50° C., for example) at time intervals (from 5 seconds to 15 minutes). Once the desired temperature or "hold temperature" is reached, which will vary for the particular metals, the compact is maintained at the hold temperature from about 1 hour to about 10 hours or from about 2 hours to about 6 hours to create the metallurgical bonds between the metal powder particles. The use of temperature intervals can allow for the elimination of separate steps or separate ovens used to remove the spacing agent and the non-polar liquid binder, if used. In various aspects, the step of sintering the compact includes sintering adjacent particles of the porous metal structure to one another and concurrently sintering the porous metal structure to the metal base, providing an integral subassembly.

Once sintered, the subassembly is aligned with a metal substrate portion of an implant, in step 108. As discussed above, the metal substrate may be provided on certain portions of the implant, or in other embodiments, the metal substrate may be on an entirety of the implant. Suitable exemplary metal substrates include Ti6Al4V, CoCrMo alloys (F75 as-cast, F75 HIP-HT, F1537 high C and low C wrought), and commercially pure titanium. In various embodiments, the metal substrate can be specially prepared prior to aligning and attaching the porous body. For example, the porous metal structure, the metal substrate portion, or both, can be machined to a desired shape prior to forming the metallurgical bond between the subassembly and the metal substrate. In certain embodiments, the machining may take place after forming the metallurgical bond. Machining may be performed with an accuracy of between about ten and twenty thousandths of an inch, depending upon the equipment. The metal substrate can be acid etched, subjected to an acid bath, grit blasted, or ultrasonically cleaned for example. Other preparations include adding channels, pits, grooves, indentations, bridges, or holes to the metal substrate. Depending on the overall geometry, these additional features may increase the attachment of the porous metal structure to the underlying metal substrate. Once aligned, a metallurgical bond is formed between the subassembly and the metal substrate portion as referenced by method box 110. In various embodiments, forming the metallurgical bond includes diffusion bonding the metal base of the subassembly to the metal substrate portion, creating an implant having a porous metal component.

After diffusion bonding, the porous metal containing implant can be quenched or rapidly cooled. Quenching can be achieved by direct quenching, fog quenching, hot quenching, interrupted quenching, selective quenching, slack quenching, spray quenching, and/or time quenching. Quenching can be performed in the diffusion bonding oven without moving the implant. For example, with fog quenching, a fog could be distributed through the oven to quench the metal and the fog could be subsequently vacuumed out. In various other embodiments, the cooling can occur for a time period of between about 3 hours and about 20 hours in an inert atmosphere.

The porous metal containing implant can also be attached as part of an orthopaedic insert, such as those disclosed in U.S. patent application Ser. No. 12/038,570 filed Feb. 27, 2008 and published as U.S. Patent Application Publication No. 2008/0147187, Bollinger et al., published Jun. 19, 2008, which is incorporated by reference herein in its entirety. The porous metal containing implant can also be used to form a geostructure, which is a three-dimensional geometric porous engineered structure that is self supporting and is constructed of rigid filaments joined together to form regular or irregular geometric shapes. The structure is described in more detail in U.S. Pat. No. 6,206,924, Timm, issued Mar. 27, 2001 which is incorporated by reference.

In various embodiments, optional agents can be coated onto or in a surface of the porous metal component of the implant. Such optional materials include ceramics, polymers, bone materials, blood products, bioactive materials, and combinations thereof. Such ceramics include resorbable or non-resorbable ceramic materials, such as glasses or ceramics comprising mono-, di-, tri-, α-tri-, β-tri-, and tetra-calcium phosphate, hydroxyapatite, calcium sulfates, calcium oxides, calcium carbonates, magnesium calcium phosphates, phosphate glass, bioglass, and mixtures thereof. Polymers include resorbable or non-resorbable polymers, such as polyhydroxyalkanoates, polylactones and their copolymers. Such polymers include poly(L-lactic acid) (PLLA), poly(D,L-lactide), poly(lactic acid-co-glycolic acid), 50/50 (DL-lactide-co-glycolide), polydioxanone, polycaprolactone and co-polymers and mixtures thereof such as poly(D,L-lactide-co-caprolactone). Bone products include bone powder and demineralized bone. Blood products include blood fractions and other blood derived materials, such as platelet rich plasma. Bioactive agents useful herein include organic molecules, proteins, peptides, peptidomimetics, nucleic acids, nucleoproteins, antisense molecules, polysaccharides, glycoproteins, lipoproteins, carbohydrates and polysaccharides, botanical extracts, and synthetic and biologically engineered analogs thereof, living cells such as stem cells (e.g., adipose derived stem cells) chondrocytes, bone marrow cells, viruses and virus particles, natural extracts, and combinations thereof. Specific examples of bioactive materials include hormones, antibiotics and other antiinfective agents, hematopoietics, thrombopoietics, agents, antiviral agents, antiinflammatory agents, anticoagulants, therapeutic agents for osteoporosis, enzymes, vaccines, immunological agents and adjuvants, cytokines, growth factors, cellular attractants and attachment agents, gene regulators, vitamins, minerals and other nutritionals, nutraceuticals and combinations thereof. For example, the optional material may be a resorbable ceramic, resorbable polymer, antimicrobial, demineralized bone, blood product, stem cell, growth factor or mixture thereof. In various embodiments the optional materials facilitate ingrowth of new tissue into the porous metal implant.

Figure 2A:
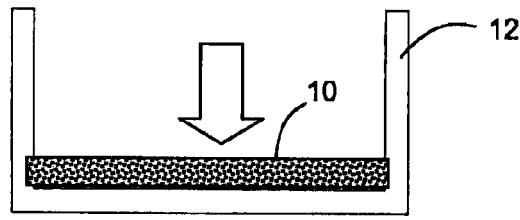
FIGS. 2A-2F illustrate certain embodiments of making a compact and subassembly of the present technology including a porous metal structure and a metal base.
Figure 2B:
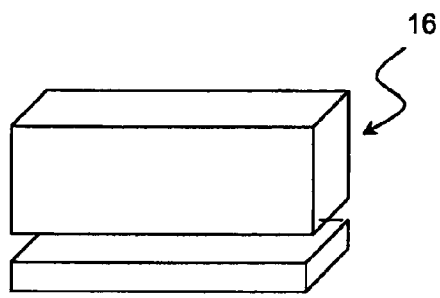
Figure 2C:
Figure 2D:
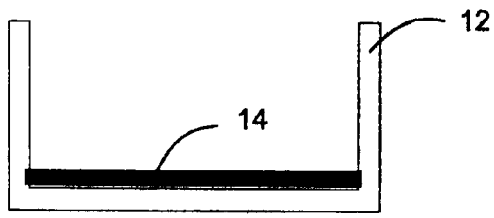
Figure 2E:
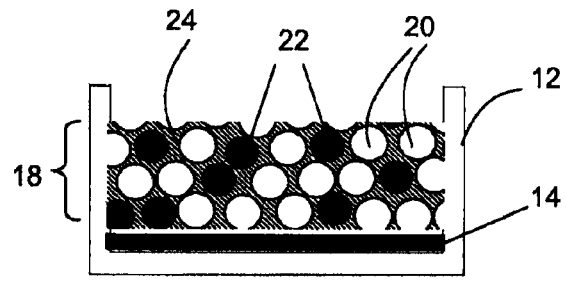
Figure 2F:
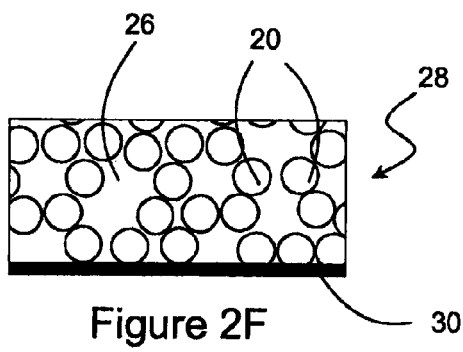

FIGS. 2A-2F illustrate certain embodiments of making a compact and subassembly of the present technology including a porous metal structure and a metal base. In various embodiments, the metal base can be provided as a layer of powder metal material. As shown in FIG. 2A, a layer of biocompatible metal powder 10 can be added to a suitable mold 12 and is compressed and/or sintered to form a substantially non-porous metal base 14 as shown in FIG. 2C. In another embodiment, as shown in FIG. 2B, the metal base 14 can be provided as a solid layer taken from a solid block of metal 16. Once the metal base 14 is obtained (from any method), it can be placed in a suitable mold 12, as shown in FIG. 2D. The loose powder mixture is then prepared and can be spread in the mold 12 on top of the metal base 14 forming a secondary layer 18 that can include metal powder 20, spacing agent 22, and an appropriate binder 24 as shown in FIG. 2E. A compressive force can then be applied to the mold contents, thereby compressing the loose powder mixture of the secondary layer 18, and pressing the secondary layer 18 onto the base layer 14. The spacing agent 22 and binder 24 are subsequently removed during thermal processing, forming pores 26 in their locations and leaving a compact 28 including a porous metal structure having a thin metal backing 30 as shown in FIG. 2F. In various embodiments, the porous metal portion of the compact 18 may be provided having a thickness of between about 1 to about 5 mm (0.04 to about 0.2 inches), or between about 2 to about 4 mm (0.08 to about 0.16 inches), while the metal backing 30 can be provided having a thickness of less than about 3 mm (about 0.12 inches), or less than about 2 mm (about 0.08 inches). In certain embodiments a thickness of as little as 0.5 mm (about 0.02 inches) can be used so as to not add additional weight or take up valuable space. The compact 28 can be subsequently sintered to form a subassembly, which is then diffusion bonded to a metal substrate portion of an implant, incorporating a porous metal component with a medical implant as described above.

Figure 3A:
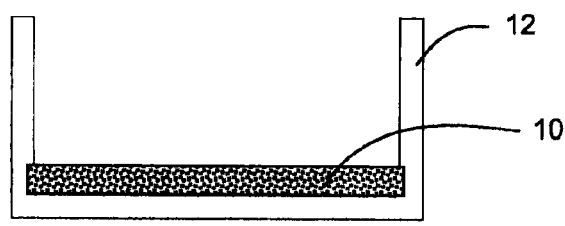
FIGS. 3A-3D illustrate another embodiment of making a compact and subassembly including a porous metal structure and a powder metal base.
Figures 3B, 3C:
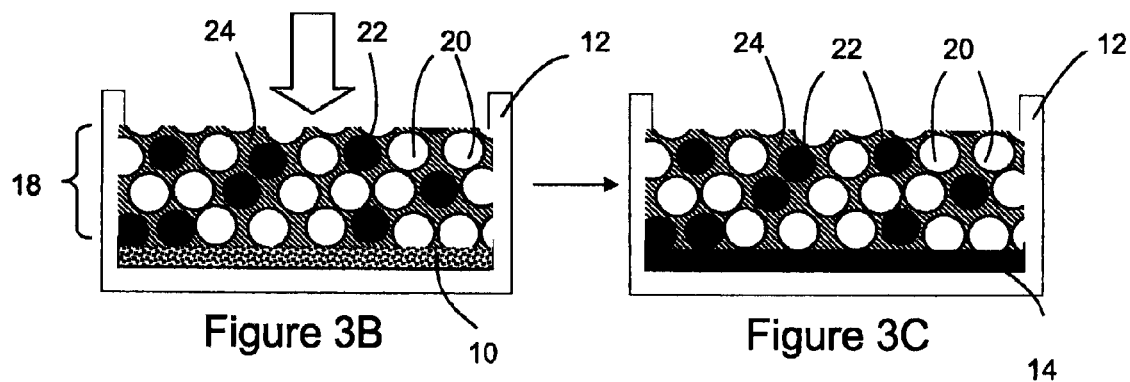
Figure 3D:
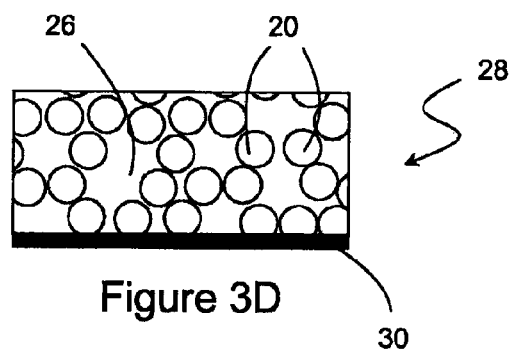

FIG. 3A-3D illustrate another embodiment of making a compact and subassembly including a porous metal structure and a powder metal base. As shown in FIG. 3A, a mold 12 is provided with a layer of biocompatible metal powder 10 to form a base layer. Prior to compressing the base layer, the loose powder mixture is prepared and spread into the mold 12 on top of the metal powder 10, forming a secondary layer 18 that can include metal powder 20, spacing agent 22, and an appropriate binder 24 as shown in FIG. 3B. Thereafter, the compressive force can be applied to the mold contents, compressing the loose powder mixture of the secondary layer 18, compressing the loose metal powder 10 of the base layer, and pressing the secondary layer 18 onto the base layer 14. The spacing agent 22 and binder 24 are subsequently removed during thermal processing, forming pores 26 in their locations and leaving a compact 28 including a porous metal structure having a thin metal backing 30 as shown in FIG. 3D. The compact can be subsequently sintered to form a subassembly, diffusion bonded to a metal substrate, and incorporated into a medical implant as described above.

Figure 4A:
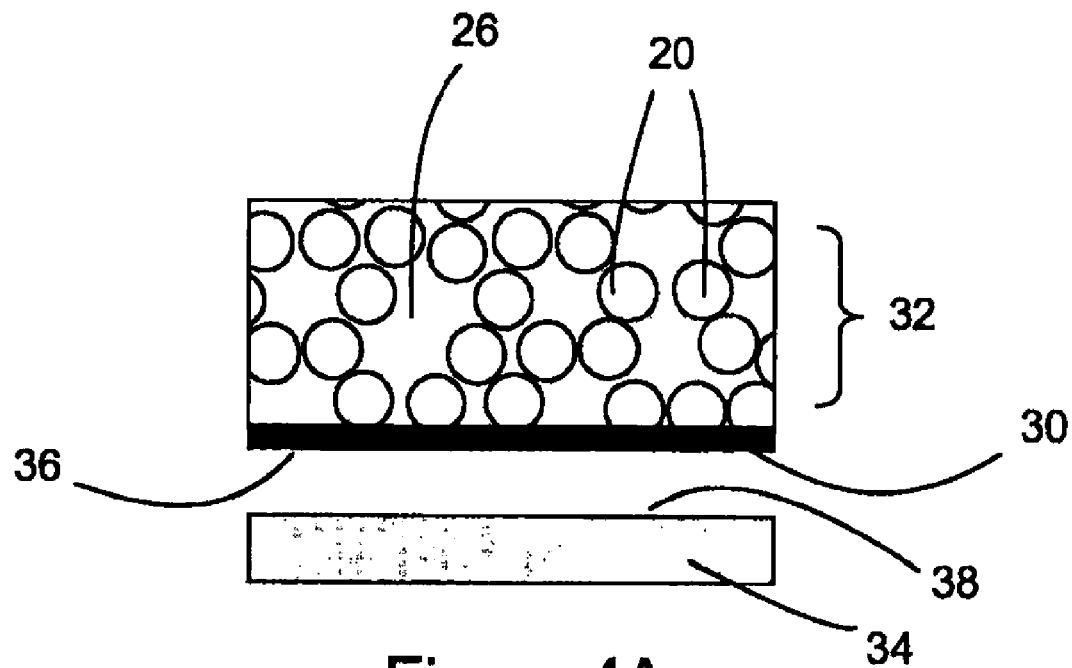
FIGS. 4A and 4B illustrate diffusion bonding a subassembly to a metal substrate.
Figure 4B:
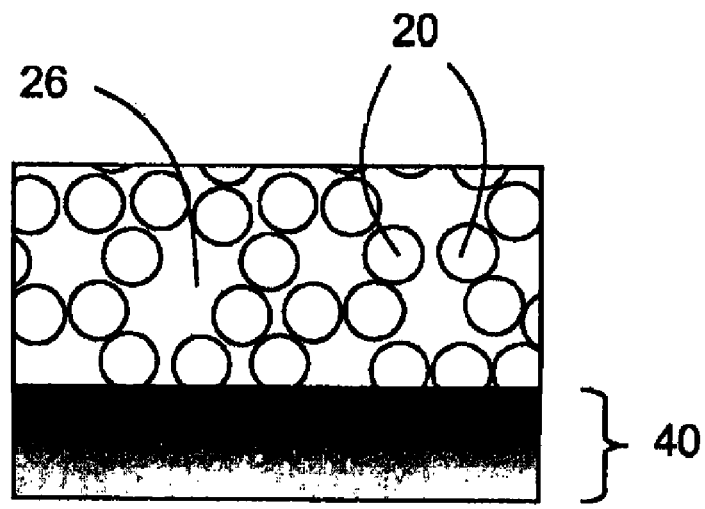

FIGS. 4A and 4B illustrate diffusion bonding a sintered subassembly 32 to a metal substrate 34. As shown in FIG. 4A, the metal base 30 can include a solid, or substantially non-porous, metal backing surface 36 and the metal substrate 34 can include a solid, or substantially non-porous, metal face 38. The diffusion bonding occurs at an interface created between the solid metal backing surface 36 and the solid metal face 38 and creates a uniform diffusion bond 40 extending along the entire joining interface as shown in FIG. 4B. Such diffusion bonding can occur along the entire interface and can be performed with the concurrent addition of pressure. In certain embodiments it may be desirable to maintain a compressive force of between about 1 and about 200 psi. Because bonding occurs along the entire interface, as opposed to limited contact points, the present technology may only require maintaining a compressive for of between about 10 psi and about 30 psi at the interface. For example, the pressure could be maintained at about 20 psi at the interface with favorable results.

Figure 5A:
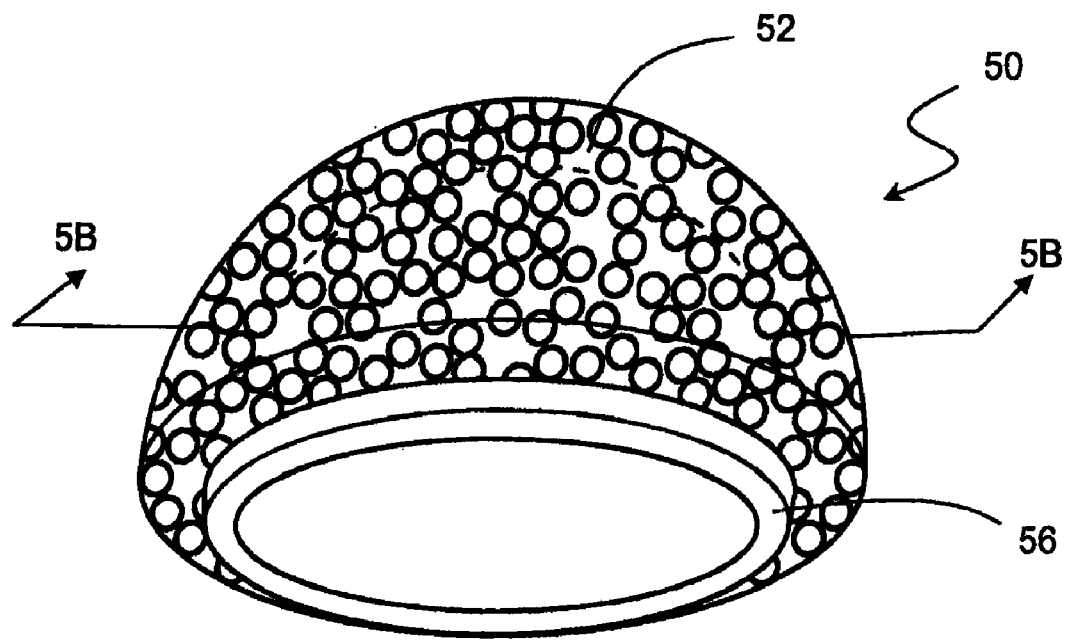
FIG. 5A is an exemplary acetubular cup shaped medical implant having a porous metal component attached thereto.
Figure 5B:
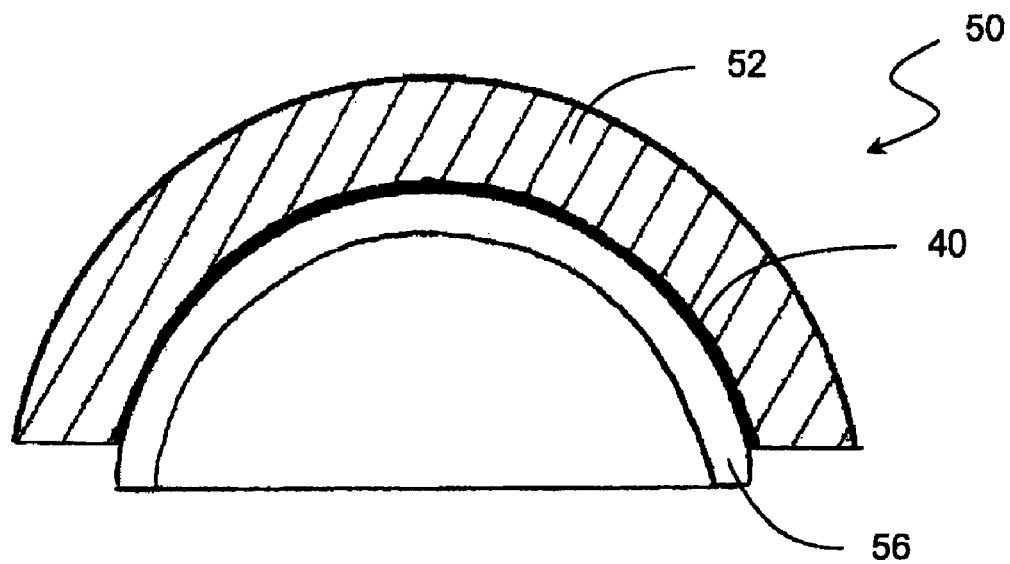
FIG. 5B is a cross section of FIG. 5A taken along the line 5B-5B.

The present technology may be used with implants having a wide range of sizes and geometrical configurations. FIG. 5A illustrates an exemplary acetubular cup medical implant 50 having a porous metal component 52 attached thereto. FIG. 5B is a cross sectional view of FIG. 5A, taken along the line 5B-5B and further illustrates the bond 40 between the metal substrate 34 of the implant 56 and the metal base 30 portion of the porous metal component 52. It is envisioned that such a porous metal component can be used with any type of implant that ultimately contacts or is near bone and would be beneficial for bone in-growth. Various other non-limiting implants include hip stems, knee femorals, primary tibial trays, wrist reconstructive systems, and various claw devices.

The embodiments described herein are exemplary and not intended to be limiting in describing the full scope of compositions and methods of the present technology. Equivalent changes, modifications and variations of embodiments, materials, compositions and methods can be made within the scope of the present technology, with substantially similar results.

What is claimed is:
1. A method for preparing an implant having a porous metal component, comprising:
   a. preparing a loose powder mixture comprising a biocompatible metal powder and a spacing agent;
   b. compressing the powder mixture onto a metal base, the metal base comprising a solid metal layer of material taken from a solid metal block;

c. removing the spacing agent to form a compact having a porous metal structure pressed on the metal base;
d. sintering adjacent powder particles of the porous metal structure to one another while concurrently sintering the porous structure to the metal base to form a subassembly;
e. aligning the subassembly with a metal substrate component; and
f. forming a metallurgical bond by diffusion bonding the metal base of the subassembly and the metal substrate component to form an implant.

2. The method of claim 1, wherein the metal base comprises a metal backing surface, the metal substrate component comprises a metal face, and the diffusion bonding occurs at an interface between the metal backing surface and the metal face.

3. The method of claim 1, wherein the biocompatible metal powder is selected from the group consisting of titanium, titanium alloys, cobalt, cobalt alloys, chromium, chromium alloys, tantalum, tantalum alloys, iron alloys, stainless steel, and mixtures thereof.

4. The method of claim 1, wherein the spacing agent comprises ammonium bicarbonate and removing the spacing agent comprises heating the powder mixture.

5. The method of claim 1, wherein compressing the powder mixture onto the metal base comprises applying an isostatic pressing technique at ambient temperature.

6. The method of claim 1, wherein the porous metal structure and the metal base have the same chemical composition.

7. The method of claim 1, further comprising machining one or both of the porous metal structure and the metal substrate, prior to forming the metallurgical bond between the subassembly and the metal substrate.

8. The method of claim 1, further comprising machining one or both of the porous metal structure and the metal substrate, after forming the metallurgical bond between the subassembly and the metal substrate.

9. The method of claim 1, further comprising coating at least a surface of the porous metal implant with material selected from the group consisting of resorbable ceramics, resorbable polymers, antimicrobials, demineralized bone, blood products, stem cells, growth factors, and mixtures thereof.

10. A method for preparing an implant having a porous metal component, comprising:
   a. preparing a loose powder mixture comprising a biocompatible metal powder and a spacing agent;
   b. compressing the powder mixture onto a solid metal base defining a metal surface;
   c. heating the compressed powder mixture and defining a plurality of pores therein to form a compact;
   e. sintering the compact to form a subassembly comprising a porous metal structure having a non-porous solid metal backing;
   f. aligning the solid metal backing of the subassembly with a metal substrate component; and
   g. diffusion bonding the solid metal backing to the metal substrate component to form an implant.

11. The method of claim 10, further comprising cooling the implant for a time period of from about 3 hours to about 20 hours in an inert atmosphere after the diffusion bonding.

12. The method of claim 10, wherein the diffusion bonding occurs along an interface between the non-porous solid metal backing and the metal substrate and comprises maintaining a compressive force of about 20 psi at the interface.

13. The method of claim 10, comprising providing the solid metal backing with a final thickness of about 0.5 mm.

14. A method for preparing an implant having a porous metal component, comprising:
   a. placing a base layer comprising a biocompatible solid metal layer into a mold;
   b. preparing a loose powder mixture of a biocompatible metal powder and a spacing agent;
   c. forming a secondary layer by spreading the loose powder mixture in the mold on top of the base layer;
   d. applying a compressive force to the mold thereby compressing the loose powder mixture of the secondary layer, and pressing the secondary layer onto the base layer;
   e. removing the spacing agent, defining a plurality of pores within the secondary layer;
   f. sintering the mold contents, including sintering adjacent powder particles of the secondary layer to one another while concurrently sintering the secondary layer to the base layer to form a subassembly including a porous metal structure having a solid metal backing; and
   g. diffusion bonding the solid metal backing of the subassembly to a metal substrate component of an implant, forming an implant.

15. The method of claim 14, wherein the steps of removing the spacing agent and sintering the mold contents are carried out in a vacuum environment.

16. The method of claim 14, wherein diffusion bonding the solid metal backing of the subassembly to a metal substrate component of an implant comprises maintaining a compressive force of between about 10 psi and about 30 psi along an interface between the solid metal backing of the subassembly and the metal substrate component.

17. The method of claim 1, wherein forming the metallurgical bond by diffusion bonding the metal base of the subassembly and the metal substrate component comprises maintaining a compressive force of between about 10 psi and about 30 psi along an interface between the metal base of the subassembly and the metal substrate component.

* * * * *